(12) United States Patent  (10) Patent No.: US 8,468,634 B2
Iwahori et al.  (45) Date of Patent: Jun. 25, 2013

(54) ELECTRIC TOOTHBRUSH

(75) Inventors: Toshiyuki Iwahori, Mishima-gun (JP); Jun Shimoyama, Uji (JP)

(73) Assignee: OMRON Healthcare Co., Ltd., Kyoto (JP)

( * ) Notice: Subject to any disclaimer, the term of this patent is extended or adjusted under 35 U.S.C. 154(b) by 353 days.

(21) Appl. No.: 12/921,424

(22) PCT Filed: Mar. 16, 2009

(86) PCT No.: PCT/JP2009/055008
§ 371 (c)(1),
(2), (4) Date: Sep. 8, 2010

(87) PCT Pub. No.: WO2009/116481
PCT Pub. Date: Sep. 24, 2009

(65) Prior Publication Data
US 2011/0005015 A1    Jan. 13, 2011

(30) Foreign Application Priority Data
Mar. 18, 2008   (JP) ................................. 2008-069405

(51) Int. Cl.
*A61C 17/22* (2006.01)
(52) U.S. Cl.
USPC ........................................... 15/22.1; 15/22.2
(58) Field of Classification Search
USPC ......................... 15/22.1, 22.2; 433/118, 119
See application file for complete search history.

(56) References Cited

U.S. PATENT DOCUMENTS

| 8,046,861 | B2 * | 11/2011 | Joseph ........................... 15/22.1 |
| 2009/0070947 | A1 | 3/2009 | Baertschi et al. |
| 2009/0188058 | A1 | 7/2009 | Schwarz-Hartmann et al. |

FOREIGN PATENT DOCUMENTS

| JP | A 4-322604 | 11/1992 |
| JP | A-07-163421 | 6/1995 |
| JP | A-08-140738 | 6/1996 |
| JP | A-2003-210492 | 7/2003 |
| JP | A 2007-61209 | 3/2007 |
| WO | WO 2007/085289 A1 | 8/2007 |
| WO | WO 2007/107274 A1 | 9/2007 |

OTHER PUBLICATIONS

International Search Report issued in Application No. PCT/JP2009/055008; Dated May 26, 2009 (With Translation).
Russian Office Action issued in Application No. 2010142276/14(060767); Dated May 25, 2011 (With Translation).
Sep. 15, 2011 Office Action issued in Russian Patent Application No. 2010142276/14(060767) (with translation).

* cited by examiner

*Primary Examiner* — Shay Karls
(74) *Attorney, Agent, or Firm* — Oliff & Berridge, PLLC

(57) ABSTRACT

An electric toothbrush includes a driving source, a vibrating member having a brush, a transmission mechanism for converting output of the driving source into vibration of the vibrating member, and control means for controlling output of the driving source. The control means has a plurality of operation modes for allowing the brush to perform a predetermined operation. The plurality of control modes are switched at high speed to allow brushing using a transient state at a time of operation mode switching. It is suitable to switch at high speed between operation modes using two resonance points in which resonance occurs in different directions. Accordingly, the electric toothbrush is improved in plaque removing power and sense of medical treatment.

17 Claims, 11 Drawing Sheets

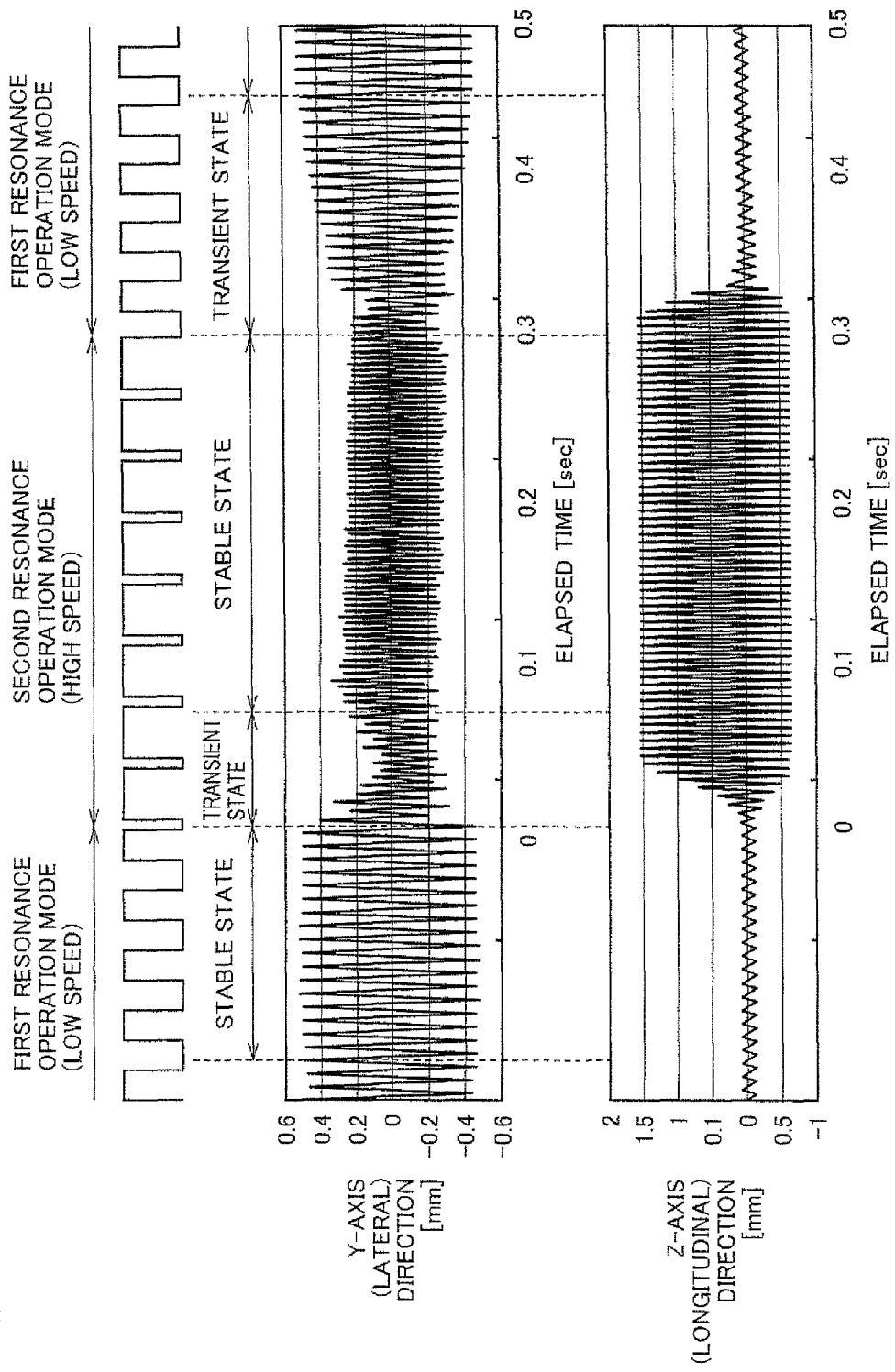

ELECTRIC TOOTHBRUSH

TECHNICAL FIELD

The present invention relates to an electric toothbrush.

BACKGROUND ART

There is known an electric toothbrush of a type which performs toothbrushing (removing plaque) by placing a fast-vibrating brush against a tooth surface. For the electric toothbrush of this type, a variety of driving mechanisms and driving methods are proposed with the aim of improving plaque removing power and improving sense of medical treatment.

For example, an electric toothbrush is commercially available which uses a technique of maximizing a frequency amplitude characteristic using mechanical resonance.

Patent Document 1 discloses an electrical toothbrush in which the motor of the electric toothbrush is switched between forward rotation and backward rotation at intervals of 1-10 seconds. When switching takes place about once to five times, the operation of the brush is temporarily stopped or is changed in strength, thereby allowing the users to grasp the time during which they brush their teeth.

Furthermore, there exists an electric toothbrush having a massage mode in which the frequency of the electric toothbrush is successively changed.

Patent Document 1: Japanese Patent Application National Publication No. 8-140738

DISCLOSURE OF THE INVENTION

Problems to be Solved by the Invention

In the aforementioned conventional technique, although control is performed for switching operation mode, the operation mode switching cycle is long and therefore the resulting plaque removing power is only equivalent to the one obtained by alternating between operation modes.

An object of the present invention is to provide a technique for further improving plaque removing power and sense of medical treatment of an electric toothbrush.

A further object of the present invention is to provide a technique for further improving plaque removing power and sense of medical treatment of an electric toothbrush without complicated structure, cost increase, and increased power consumption.

Means for Solving the Problems

In order to achieve the above-noted objects, the present invention employs the following configuration.

An electric toothbrush in accordance with the present invention includes: a driving source; a vibrating member having a brush; a motion transmission mechanism for converting output of the driving source into vibration of the vibrating member; and control means for controlling output of the driving source. The control means performs control of repeating (switching) a driving frequency of the vibrating member at high speed between a plurality of different frequencies to utilize brushing during transition at said switches of said driving frequency.

In driving the vibrating member, the brush makes a steady movement in a stable state while the brush makes such an irregular movement in a switching period (transient state) that cannot be achieved in a stable state. This irregular brush movement presumably provides higher plaque removing power. Then, the control means in the present invention increases the proportion of the transient state in the toothbrushing time by switching the driving frequencies at high speed thereby to allow brushing with such an irregular brush operation in the transient state. Therefore, according to the electric toothbrush in the present invention, high plaque removing power can be achieved and sense of medical treatment can be improved.

Furthermore, in the present invention, since the irregular brush operation as described above is realized only by control of output of the driving source, no special mechanism or part is required for the driving system and the transmission system. Therefore, complication of the structure and cost increase of the brush are not caused.

The control means in the present invention may alternately switch between two driving frequencies or may switch three or more driving frequencies in a predetermined order or at random.

Suitably, at least one of the plurality of different frequencies is a resonance frequency of the vibrating member. Furthermore, it is suitable that a plurality of resonance frequencies are included in a plurality of different frequencies. This is because the amplitude of the brush can be increased by utilizing resonance.

Here, the vibrating member in the present invention has a first resonance point in which the brush resonates in a first direction and a second resonance point in which the brush resonates in a second direction. Suitably, the control means has a first operation mode in which output of the driving source is controlled such that resonance in the first direction is produced and a second operation mode in which output of the driving source is controlled such that resonance in the second direction is produced, and switches the first and second operation modes at high speed.

The amplitude of the brush is greater in an operation mode using resonance (hereinafter referred to as "resonance operation mode") such as the above-noted first and second operation modes than in an operation mode without using resonance (hereinafter referred to as "normal operation mode"). As the amplitude of the brush in a stable state is large, the amplitude of the brush in a transient state is also large. Therefore, if the resonance operation mode is included in at least one of the operation modes before and after switching, the amplitude of the brush can be made large both in the stable state and in the transient state (that is, over the entire treatment period), thereby achieving higher plaque removing effect and sense of medical treatment. Furthermore, the use of the resonance phenomenon can realize an increased amplitude (improved plaque removing power) with power consumption equivalent to that in the normal operation mode and is thus effective.

Further suitably, the control means in the present invention alternately switches the first operation mode and the second operation mode. Two resonance operation modes having a large brush amplitude are repeated, so that the amplitude of the brush in the transient state is also larger, resulting in high plaque removing power.

Preferably, the first direction is a direction parallel to a brush face, and the second direction is a direction vertical to the brush face. Here, the "brush face" refers to a virtual plane orthogonal to the fibers of the brush and positioned at the tip end portion of the fibers. With the resonance in the first direction, the bristles of the brush move at short strokes in a direction parallel to a treated part, so that a high brushing effect for periodontal pockets can be expected. With the resonance in the second direction, the bristles of the brush move at short strokes in a direction vertical to a treated part, so that a high brushing effect for between teeth, periodontal pockets, and tooth surfaces can be expected. Then, an irregular movement in which those first and second directions are combined is made in the transient state, so that the effects of both the operation modes can be achieved at the same time.

Preferably, the first resonance point is characterized by being dependent on the motion transmission mechanism, and the second resonance point is characterized by being dependent on the brush.

Preferably, the control means senses a load acting on the brush and adjusts output of the driving source according to the sensed load. This is because the vibration characteristics of the vibrating member vary depending on the load acting on the brush.

Preferably, the motion transmission mechanism is contained in the vibrating member and the vibrating member is attached to an electric toothbrush body with an elastic member interposed. According to this configuration, while the vicinity of the brush vibrates efficiently due to inclusion of the motion transmission mechanism in the vibrating member, vibration of the vibrating member is hardly transferred to the electric toothbrush body because of interposition of the elastic member, thereby improving usability.

Preferably, the driving source is a motor, the motion transmission mechanism is an eccentric shaft coupled to a rotation shaft of the motor, and the vibrating member includes a stem having a bearing of said eccentric shaft. In the electric toothbrush having such driving principle, the vibrating member (brush) vibrates two-dimensionally in a plane vertical to the rotation shaft. Then, respective resonances appear in two directions approximately orthogonal to each other in the vibrating plane. Those two directions can be used as the above-noted first and second directions.

It is noted that the operation modes may not use resonance as long as the trajectory of the brush operation corresponding to the driving frequency before switching is different from the trajectory of the brush operation corresponding to the driving frequency after switching. This is because if the trajectories of the brush operation are different between before and after switching, the trajectory of the brush is irregular in the transient state thereby improving the plaque removing effect.

Suitably, the control means in the present invention switches the driving frequency at high speed such that a transient state period is one third or more of a stable operation period, that is, a proportion of the transient state period in the entire operation period is one quarter or more. Further suitably, the driving frequency is switched at high speed such that the transient state period is equal to or longer than the stable operation period, that is, the proportion of the transient state period in the entire operation period is one half or more. It is noted that here the stable operation period is a period during which an operation of the brush is stable and the transient state period is a period from switching of a driving frequency until an operation of the brush becomes stable.

The present invention can be configured with any possible combination of the means and processes as mentioned above.

Effects of the Invention

The present invention provides improvement in plaque removing power and sense of medical treatment of an electric toothbrush. Moreover, the present invention does not involve a complicated structure, a cost increase, and increased power consumption.

BRIEF DESCRIPTION OF THE DRAWINGS

FIG. 7 is a diagram showing trajectories of the brush in the Y-axis (lateral) direction and the Z-axis (longitudinal) direction in a transient state.

DESCRIPTION OF THE REFERENCE SIGNS 1 electric toothbrush body, 10 motor, 11 rotation shaft, 12 driving circuit, 121 memory, 122 timer, 123 current sensing circuit, 13 rechargeable battery, 14 coil, 2 vibrating member, 20 stem portion, 200 stem, 201 holder, 202 elastic member, 202A protrusion portion, 203 bearing, 21 brush part, 210 brush, 30 eccentric shaft, 300 weight, 40 trajectory, S switch

BEST MODES FOR CARRYING OUT THE INVENTION

In the following, suitable embodiments of the present invention will be described with reference with the figures in detail by way of illustration.

First Embodiment

<Structure of Electric Toothbrush>

Figure 1:
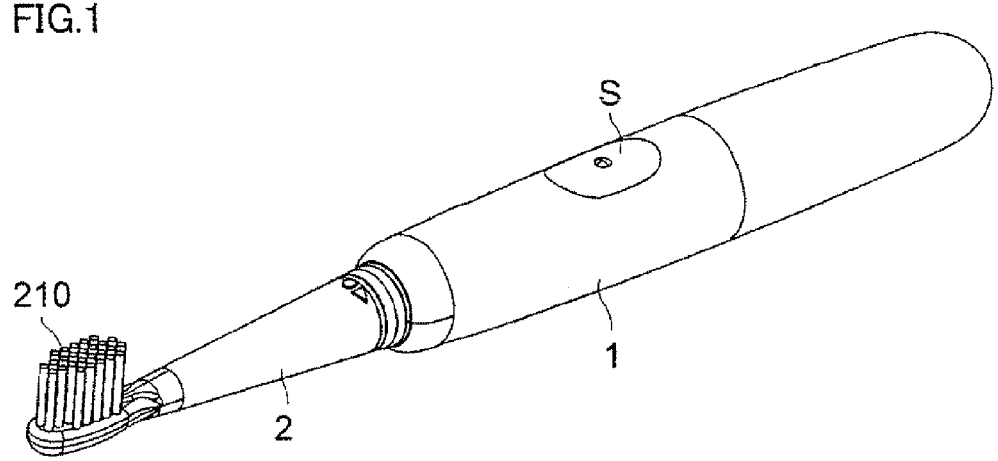
FIG. 1 is a perspective view showing an external view of an electric toothbrush.
Figure 2:
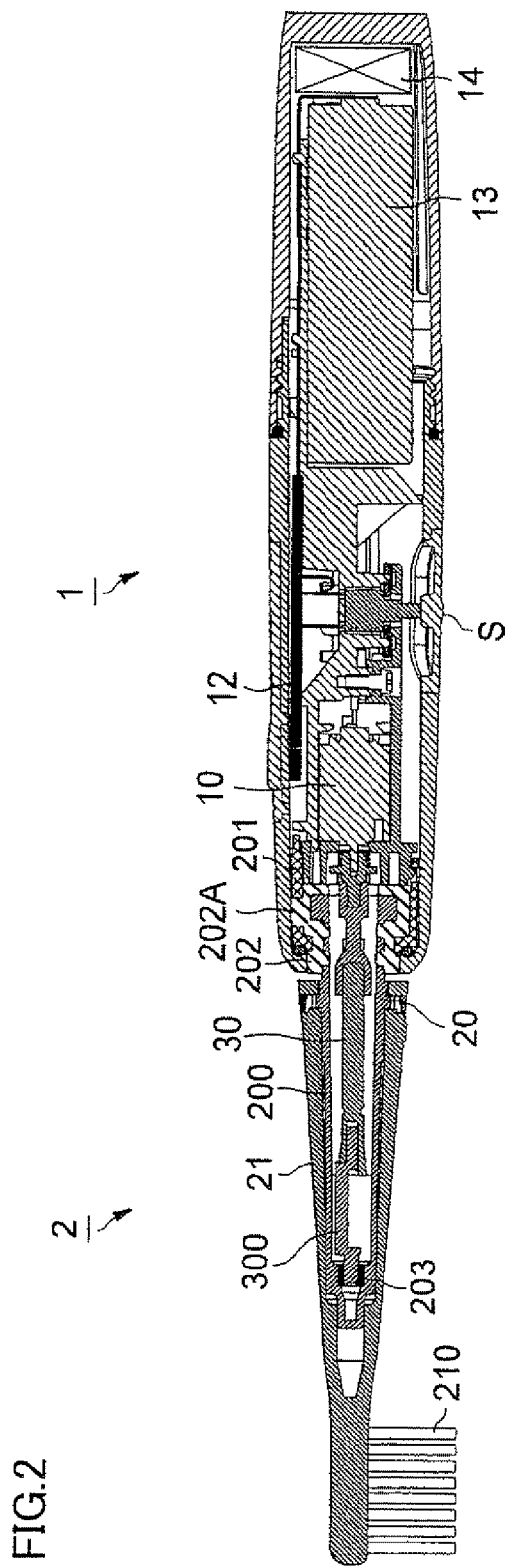
FIG. 2 is a cross-sectional view showing an internal structure of the electric toothbrush.
Figure 3:
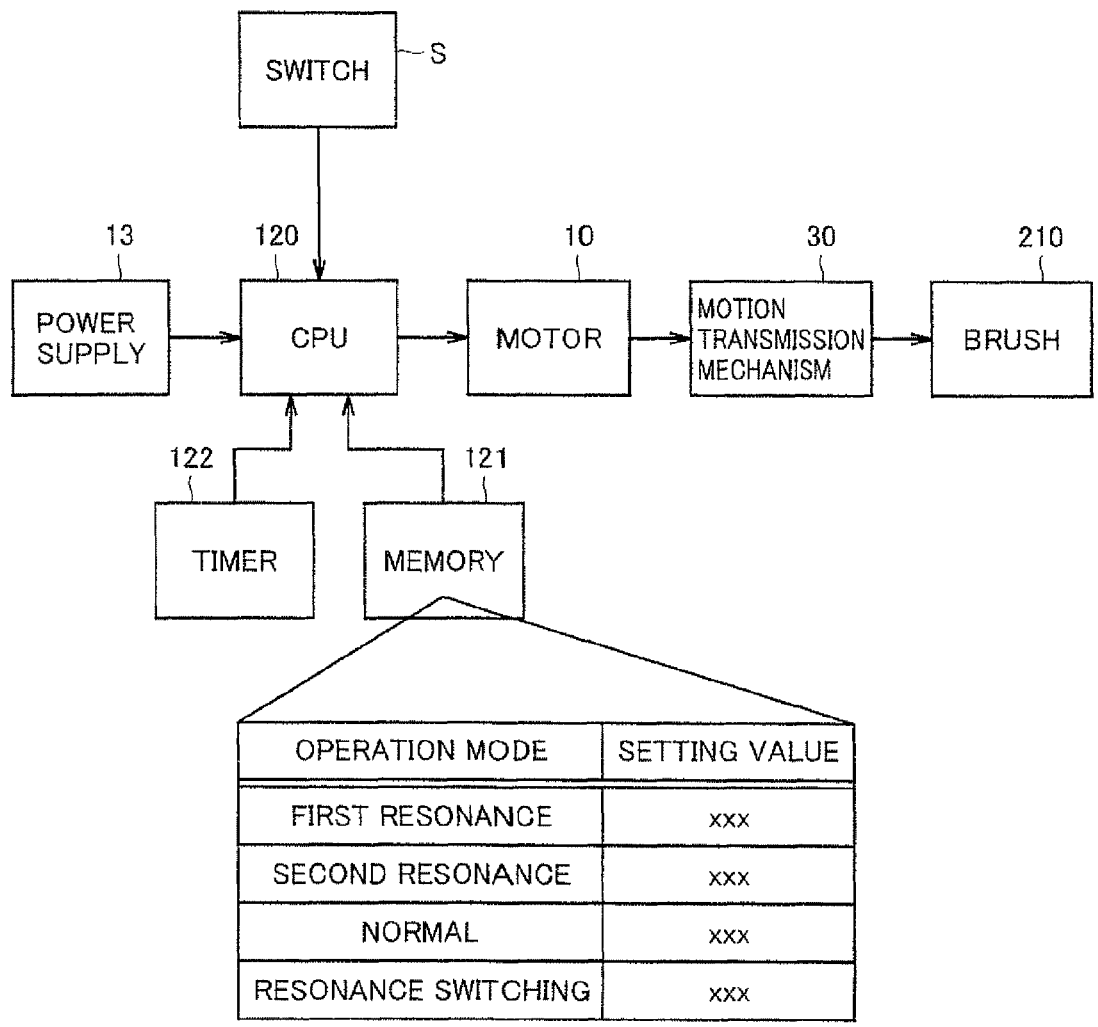
FIG. 3 is a block diagram in accordance with a first embodiment.

Referring to FIG. 1, FIG. 2, and FIG. 3, a structure of an electric toothbrush will be described. FIG. 1 is a perspective view showing an external view of the electric toothbrush, FIG. 2 is a cross-sectional view showing an internal structure of the electric toothbrush, and FIG. 3 is a block diagram.

The electric toothbrush includes an electric toothbrush body 1 (hereinafter simply referred to as "body 1") containing a motor 10 serving as a driving source, and a vibrating member 2 having a brush 210. Body 1 has a generally cylindrical shape and also serves as a handle portion for the user to grip by hand in brushing his/her teeth.

Body 1 is provided with a switch S for turning on/off the power and for switching operation mode. Provided in the inside of body 1 are motor 10 serving as a driving source, a driving circuit 12 for controlling the rotational speed of motor 10, a rechargeable battery 13 serving as a power supply of 2.4 V, a coil 14 for charging, and the like. In order to charge rechargeable battery 13, body 1 is simply placed on a charger (not shown) so that non-contact charging is realized by electromagnetic induction. As shown in FIG. 3, driving circuit 12 has a CPU (Central Processing Unit) 120, a memory 121 for storing programs and a variety of setting values, a timer 122, and the like.

Vibrating member 2 includes a stem portion 20 fixed to the body 1 side and a brush part 21 attached to this stem portion 20. A brush 210 is embedded in the tip end of brush part 21. Brush part 21 is a consumable and is thus configured to be removable from stem portion 20 so that it can be replaced with a new one.

Stem portion 20 is configured with a stem 200 and a holder 201 made of a resin material, and an elastic member 202 made of elastomer. Elastic member 202 is preferably formed integrally with stem 200 and holder 201 by insert molding. Elastic member 202 is interposed between stem 200 and holder 201 and includes a plurality (for example, three) of protrusion portions 202A which protrude through a plurality of through-holes provided at holder 201. Stem portion 20 is positioned with respect to the outer case of body 1 by three-point contact of three protrusion portions 202A of elastic member 202. In this manner, vibrating member 2 in the present embodiment is mounted on body 1 with elastic member 202 interposed.

Stem 200 is a tubular member which is closed at the tip end (the brush-side end) and has a bearing 203 at the tip end in the inside of the tube. A tip end of an eccentric shaft 30 coupled to a rotation shaft 11 of motor 10 is inserted in bearing 203 of stem 200. This eccentric shaft 30 has a weight 300 in the vicinity of bearing 203, and the center of gravity of eccentric shaft 30 is offset from the center of rotation. It is noted that a minute clearance is provided between the tip end of eccentric shaft 30 and bearing 203.

<Basic Operation of Electric Toothbrush>

A basic operation of the electric toothbrush will be described.

In a power-on state, CPU 120 supplies a pulse width modulation signal (PWM signal) to motor 10 to rotate rotation shaft 11 of motor 10. Eccentric shaft 30 also rotates along with the rotation of rotation shaft 11, where eccentric shaft 30 moves such that it turns around the center of rotation because the center of gravity is offset. Therefore, the tip end of eccentric shaft 30 repeatedly collides against the inner wall of bearing 203 to allow stem 200 and brush part 21 attached thereto to vibrate at high speed. In other words, eccentric shaft 30 acts as a motion transmission mechanism (motion conversion mechanism) for converting output (rotation) of motor 10 into vibration of vibrating member 2. Plaque can be removed by holding body 1 in hand and placing the fast-vibrating brush 210 against teeth. It is noted that CPU 120 monitors the operation duration time using timer 122 and automatically stops the vibration of the brush after a lapse of a prescribed time (for example two minutes).

In the electric toothbrush in the present embodiment, eccentric shaft 30 which is a motion transmission mechanism is contained in vibrating member 2, and in particular, weight 300 is arranged in the vicinity of brush 210. Therefore, the part of brush 210 can be vibrated efficiently. On the other hand, since vibrating member 2 (stem portion 20) is mounted on body 1 with elastic member 202 interposed, vibration of vibrating member 2 is hardly transferred to body 1. This can reduce vibration of body 1 and hand during brushing of teeth, thereby improving usability.

<Explanation of Vibration Characteristic>

Figure 4:
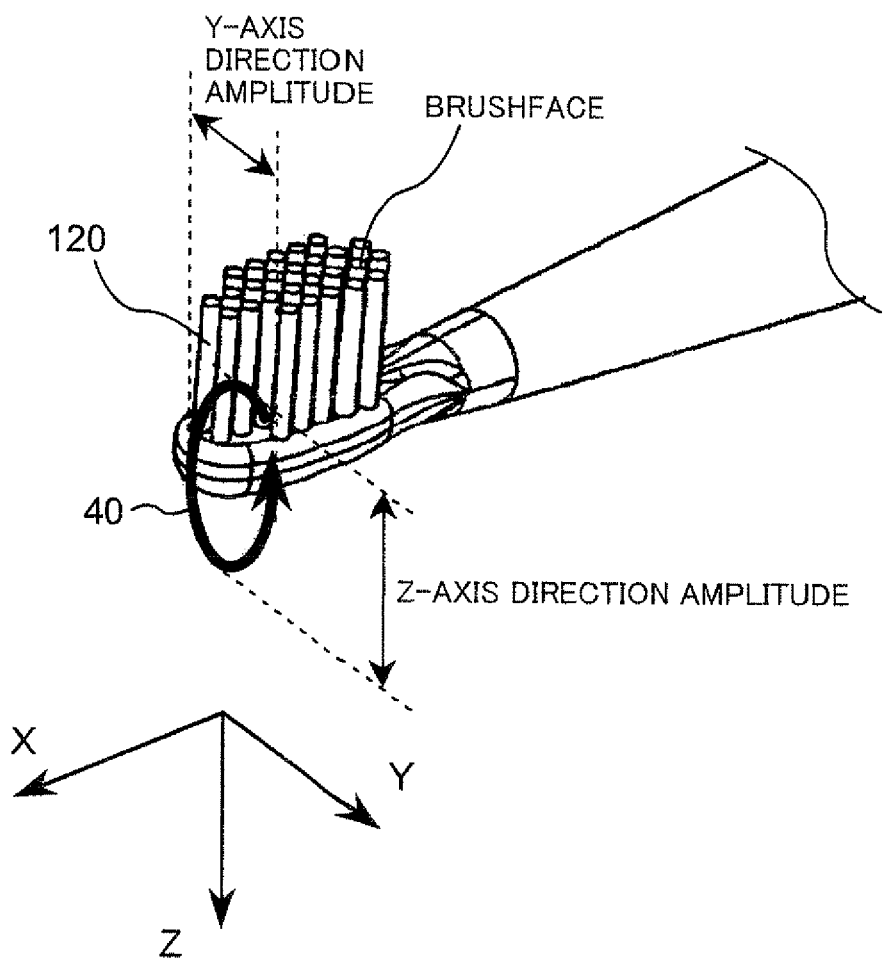
FIG. 4 is a diagram schematically showing vibration of a brush.

In the electric toothbrush in the present embodiment, the turning motion of eccentric shaft 30 is utilized to generate vibration of brush 210. In the case of such driving principle, brush 210 may vibrate two-dimensionally in the plane vertical to the rotation shaft of the motor. FIG. 4 schematically shows the trajectory of vibration of the brush (the X-axis: the motor rotation shaft, the Y-axis: the direction vertical to the rotation shaft and parallel to the brush face, the Z-axis: the direction vertical to the brush face). In the example shown in the figure, brush 210 vibrates in the YZ plane along an elliptical trajectory 40. The brush face refers to a virtual plane that is orthogonal to the fibers of the brush and is positioned at the end portion of the fibers.

Figure 5:
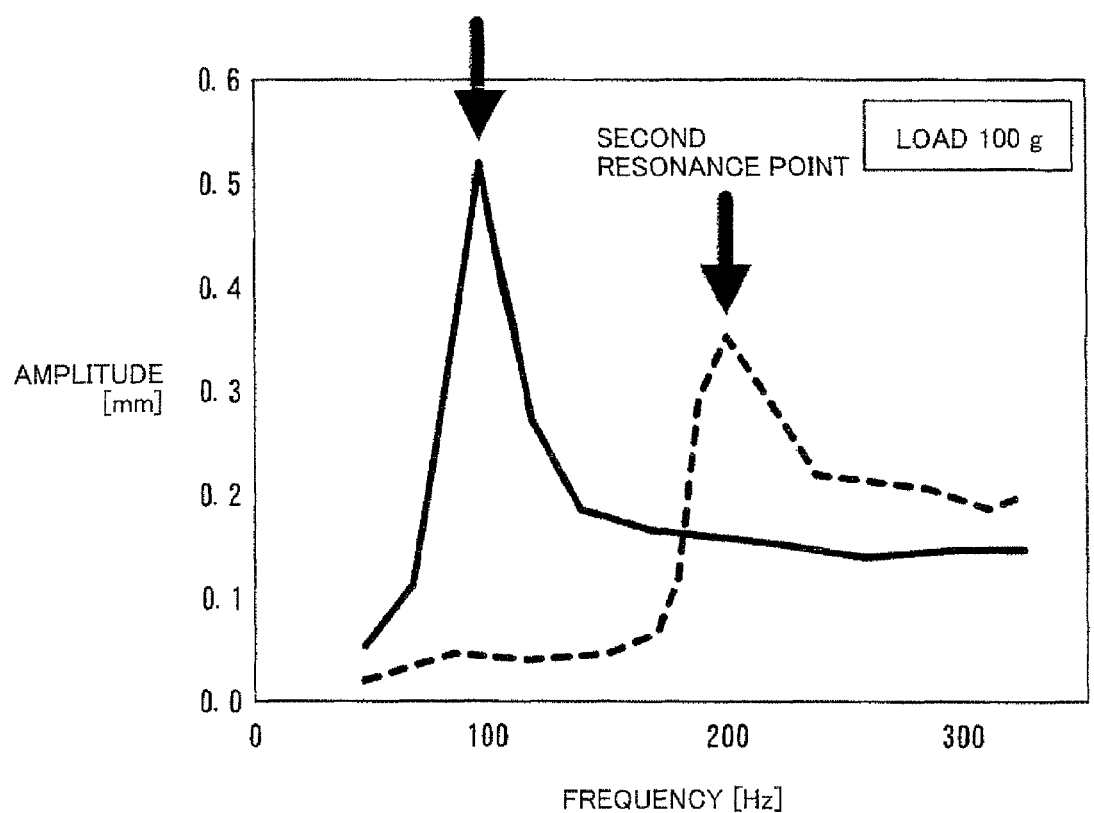
FIG. 5 is a graph showing resonance points in a case of a load 100 g.

The electric toothbrush in the present embodiment has a vibration characteristic as shown in FIG. 5. It is noted that FIG. 5 shows the relation between frequency and amplitude in a state in which a load of 100 g is applied to the brush in the Z-axis direction. The horizontal axis indicates the frequency [Hz], the vertical axis indicates the amplitude [mm], the solid line in the graph represents the amplitude in the Y-axis direction (lateral direction), and the broken line in the graph represents the amplitude in the Z-axis direction (longitudinal direction).

As can be understood from the graph in FIG. 5, the electric toothbrush in the present embodiment has at least two resonance points (resonance frequencies), where the resonance directions of those resonance points are different from each other. Specifically, at the resonance point (first resonance point: about 100 Hz) on the lower frequency side, resonance occurs in the Y-axis direction which is the resonance direction parallel to the brush face, whereas at the resonance point (second resonance point: about 200 Hz) on the higher frequency side, resonance occurs in the Z-axis direction which is a resonance direction vertical to the brush face.

The reason why a plurality of resonances that are different in direction appear may be that they are heavily dependent on the structure of the electric toothbrush or the driving principle thereof. The inventors of the present invention have repeated experiments with various eccentric shafts and brush structures and then made a finding that the first resonance point is characterized by being mainly dependent on the motion transmission mechanism and that the second resonance point is characterized by being mainly dependent on the brush. In other words, it has been found that the frequency and amplitude of the first resonance point can be adjusted by changing the structure and shape of the motion transmission mechanism (simply, the position, size, weight, etc. of the weight of the eccentric shaft), and that the frequency and amplitude of the second resonance point can be adjusted by changing the structure and shape of the brush.

In the operation mode using the first resonance point (hereinafter referred to as "first resonance operation mode"), as can be understood from FIG. 5, almost no vibration in the Z-axis direction occurs, so that the trajectory of the brush is in the form of a straight line in which it reciprocates in the Y-axis direction. In the operation mode using the second frequency point (hereinafter referred to as "second resonance operation mode"), resonance in the Z-axis direction occurs and amplitude in the Y-axis direction also appears, so that the trajectory of the brush is in the form of an ellipse having the longer axis in the Z-axis direction.

The present inventors have found that a high brushing effect for periodontal pockets can be achieved by vibration of the brush in a transient state which takes place when the first resonance operation mode and the second resonance operation mode are switched.

Figure 6:
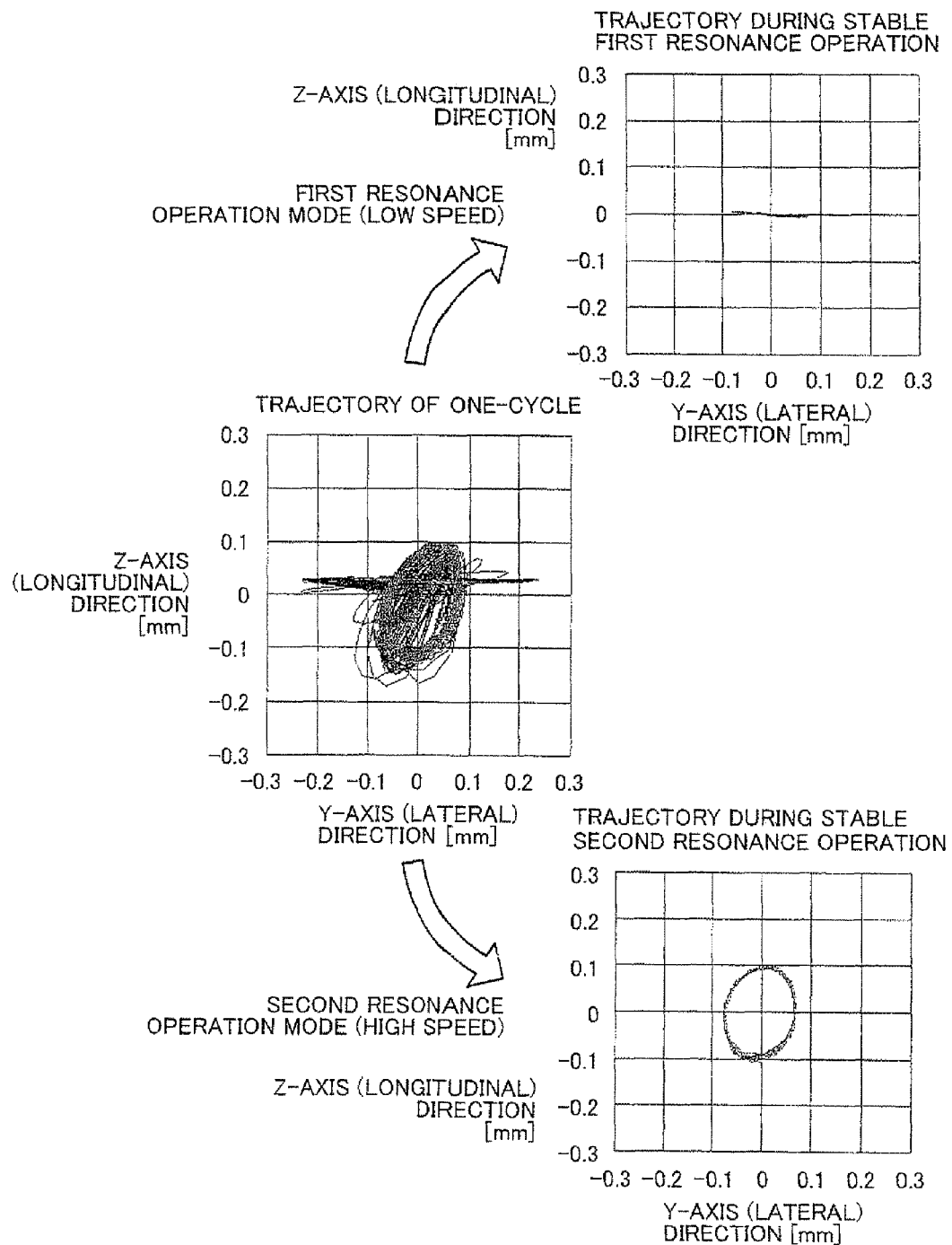
FIG. 6 is a diagram showing trajectories of the brush in a transient state.

By examining the movement of the brush when the first resonance operation mode and the second resonance operation mode are alternately switched, it has been found that the brush has the trajectory as shown in FIGS. 6 and 7. FIG. 6 is a diagram showing the trajectory of the brush in the YZ plane, and FIG. 7 is a diagram showing each of YZ components of the trajectory. In this example, the first resonance operation mode and the second resonance operation mode are alternately switched every 0.3 seconds. As shown in FIG. 7, it can be understood that when each operation mode is switched, the frequency amplitudes in the YZ-axis directions change and the brush makes an irregular movement accordingly. This irregular brush movement allows the bristles of the brush to touch the treated part from various angles, which is presumably the reason why the plaque removing effect is superior to brushing in a single direction.

It is noted that, in this example, the transient state period in which the first resonance operation mode (low frequency) is shifted to the second resonance operation mode (high frequency) is about 0.07 seconds, and the transient state period in which the second resonance operation mode is shifted to the first resonance operation mode is about 0.14 seconds. Shifting from the second resonance operation mode to the first resonance operation mode takes longer time due to the effect of inertia.

In order to enhance the plaque removing effect using the irregular brush movement in the transient state in this manner, the present inventors have conceived that the proportion of the transient state period in the brush operating period should be increased by switching operation mode at high speed.

<Description of Operation Mode>

The electric toothbrush in the present embodiment has a plurality of operation modes having respective different driving frequencies. Every time a switch S is pressed from a power-off state, operation modes are switched in order, and upon completion of one cycle, the off state returns. As shown in FIG. 3, setting values corresponding to respective operation modes are stored beforehand in memory 121. Those setting values are parameters corresponding to the respective driving frequencies of the operation modes, and their specific numerical values are determined based on the experimental results as in FIG. 5.

When operation mode is switched, CPU 120 reads the corresponding setting value from memory 121 and determines a duty ratio of a PWM signal in accordance with that value. As the duty ratio increases, the rotational speed of motor 10 becomes higher and the frequency of brush 210 also becomes higher. In this manner, in the present embodiment, driving circuit 12 acts as control means for controlling output (rotational speed) of motor 10 and the frequency of brush 210.

(1) First Resonance Operation Mode

The first resonance operation mode is an operation mode using the first resonance point. The driving frequency is set to the first resonance point (about 100 Hz) or the vicinity thereof. In the first resonance operation mode, a PWM signal having a duty ratio of about 50% is used. In the first resonance operation mode, the amplitude in the Y-axis direction (lateral direction) of brush 210 increases as compared with the normal operation mode, thereby enhancing the plaque removing effect and sense of medical treatment. In particular, in the first resonance operation mode, the bristles of brush 210 move with short strokes in the direction parallel to the treated part, so that it is presumed that a high brushing effect is achieved for periodontal pockets.

(2) Second Resonance Operation Mode

The second resonance operation mode is an operation mode using the second resonance point. The driving frequency is set to the second resonance point (about 200 Hz) or the vicinity thereof. In the second resonance operation mode, a PWM signal having a duty ratio of about 90% is used. In the second resonance operation mode, the amplitude in the Z-axis direction (longitudinal direction) of brush 210 increases as compared with the normal operation mode, thereby enhancing the plaque removing power and sense of medical treatment. In particular, in the second resonance operation mode, the bristles of brush 210 move with short strokes in the direction vertical to the treated part, so that it is presumed that a high brushing effect is achieved for between teeth, periodontal pockets, and tooth surfaces.

(3) Normal Operation Mode

The normal operation mode is an operation mode that does not use resonance. The driving frequency is set between the first resonance point and the second resonance point (for example, 150 Hz). It is noted that multiple stages of normal operation mode, such as 120 Hz, 140 Hz, 160 Hz, 180 Hz, may be set and switched by switch S. Preferably, the normal operation mode is set at a frequency lower than the first resonance point or a frequency higher than the second resonance point.

(4) Resonance Switching Operation Mode

The resonance switching operation mode is an operation mode in which the first resonance operation mode and the second resonance operation mode are alternately repeated at short time intervals. In the resonance switching operation mode, in which the first resonance operation mode and the second resonance operation mode are repeated, the duty radio of the PWM signal is calculated from the setting value of each resonance operation mode which is stored in memory 121. The setting value stored in memory 121 in the resonance switching operation mode is the operating time in each resonance operation mode.

Figure 8A:
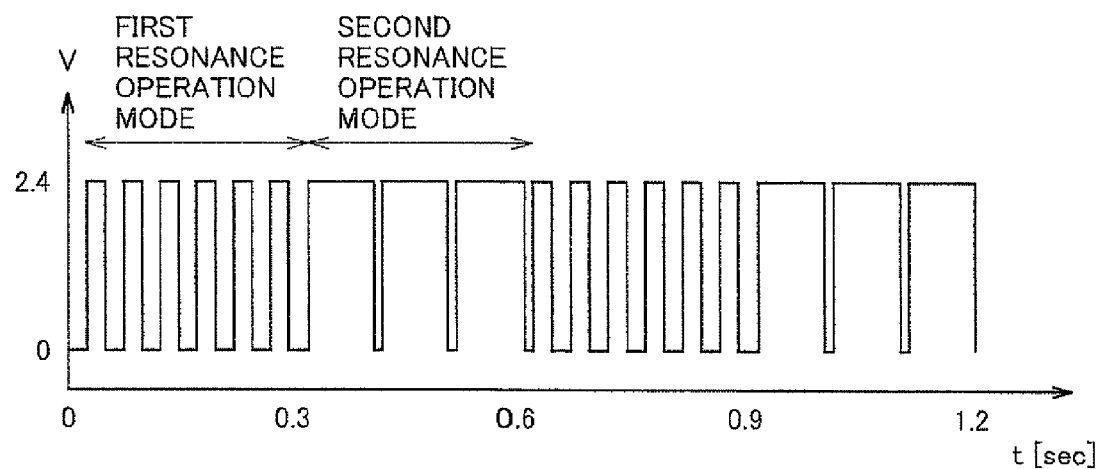
FIG. 8A is a diagram showing a waveform of a PWM signal in a resonance switching operation mode.
Figure 8B:
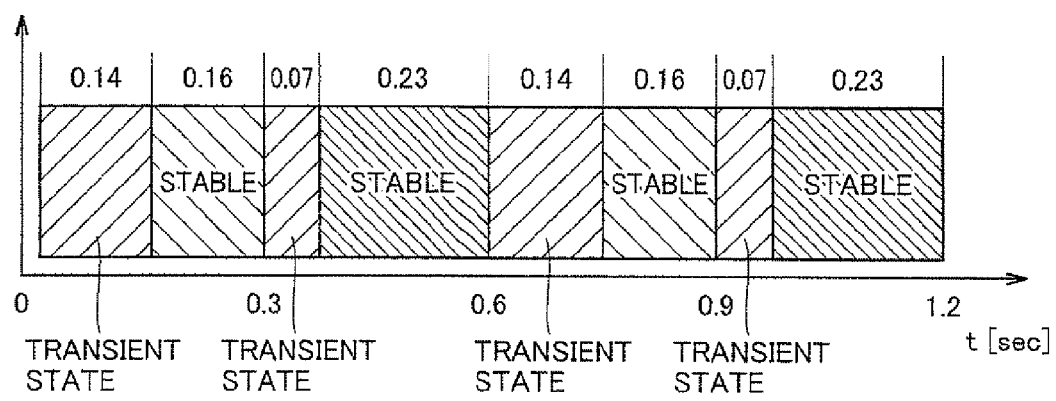
FIG. 8B is a diagram showing a brush vibration state in the resonance switching operation mode.

If the operating time in each resonance operation mode is 0.3 seconds, as shown in FIG. 8A, the output of the PWM signal is switched between the duty ratios corresponding to the first resonance operation mode and the second resonance operation mode every 0.3 seconds. Supposing that the transient state from the first resonance operation mode to the second resonance operation mode continues for about 0.07 seconds and that the transient state from the second resonance operation mode to the first resonance operation mode continues about 0.14 seconds as described above, the stable operation period in the first resonance operation mode is about 0.16 seconds and the stable operation period in the second resonance operation mode is about 0.23 seconds, as shown in FIG. 8B. The total transient state period is about 0.21 seconds and takes up about a third of the whole. In such operation mode, three kinds of brushings, namely brushings having a large amplitude in the respective stable operation periods in the first and second resonance operation modes and irregular brushing in the transient state, appear for the respective time periods equivalent to each other. Those brushings bring about the respective different types of brushing effect, so that the respective brushing effects can be obtained at the same time in the present operation mode.

It is noted that the interval of switching between the first resonance operation mode and the second resonance operation mode may not always be 0.3 seconds. For example, switching may take place at intervals of 0.2 seconds or 0.4 seconds. The operation states of the brush in the case of switching at the intervals of 0.2 seconds and 0.4 seconds are shown in FIGS. 9A and 9B, respectively.

Figure 9A:
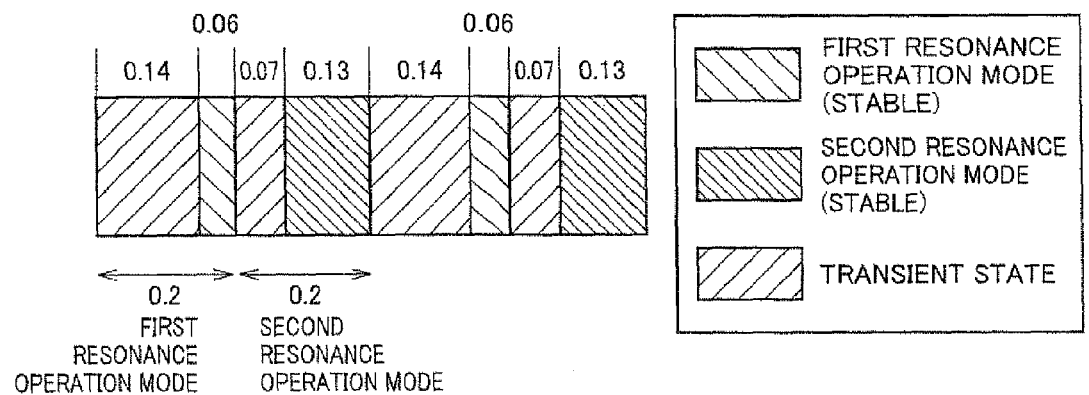
FIG. 9A is a diagram showing another example of a brush driving state in the resonance switching operation mode.

As shown in FIG. 9A, when switching takes place at intervals of 0.2 seconds, the stable operation period in the first resonance operation mode is about 0.06 seconds and the stable operation period in the second resonance operation mode is about 0.13 seconds. The total transient state period is about 0.21 seconds and takes up about a half of the whole.

Figure 9B:
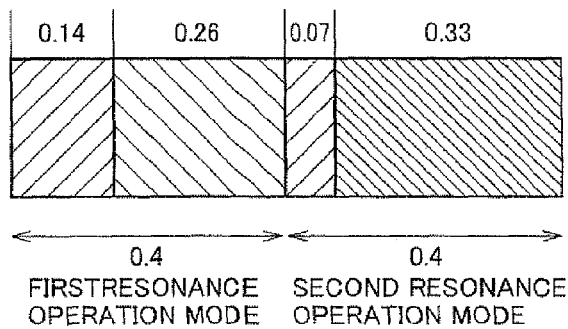
FIG. 9B is a diagram showing another example of a brush driving state in the resonance switching operation mode.

As shown in FIG. 9B, when switching takes place at intervals of 0.4 seconds, the stable operation period in the first resonance operation mode is about 0.26 seconds and the stable operation period in the second resonance operation mode is about 0.33 seconds. The total transient state period is about 0.21 seconds and takes up about a quarter of the whole.

The switching interval may be longer or shorter than the above-noted ones. However, if the switching interval is too long, the proportion of the transient state period in the total operation time becomes small, so that a sufficient plaque removing effect brought by the irregular brushing operation cannot be obtained. Conversely, when the switching interval is too short, the stable operation in the resonance operation mode is not achieved. That the operation is not stable in the resonance operation mode means that the amplitude in the transient state is not large enough and means that a sufficient plaque removing effect is not achieved.

Figure 9C:
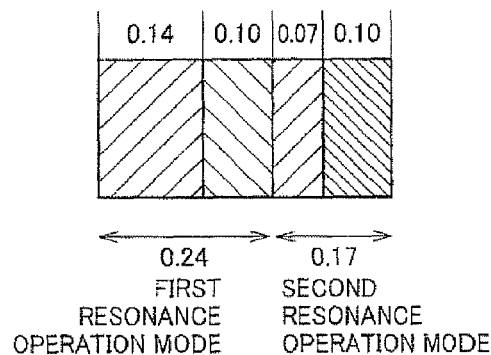
FIG. 9C is a diagram showing another example of a brush driving state in the resonance switching operation mode.

Furthermore, the switching operation interval may be varied from one resonance operation mode from another. For example, it is assumed that the operation period of the first resonance operation mode is set to 0.24 seconds and the operation period of the second resonance operation mode is set to 0.17 seconds. The operation state of the brush in this case is shown in FIG. 9C. In this setting, the stable operation period in the first resonance operation mode is about 0.10 seconds, the stable operation period in the second resonance operation mode is about 0.10 seconds, and the total transient state period is about 0.21 seconds. This is such a setting in that the ratio of the transient state period to the stable operation period is one to one and in that the stable operation periods of the first and second resonance operation periods are equal to each other.

Figure 9D:
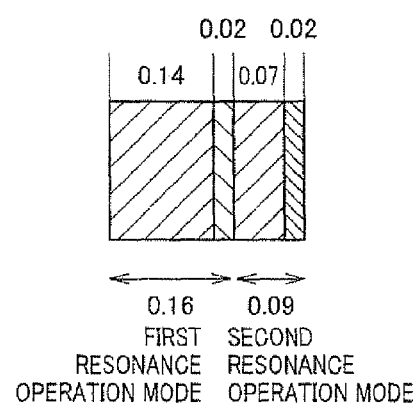
FIG. 9D is a diagram showing another example of a brush driving state in the resonance switching operation mode.

Furthermore, switching may be performed at high speed so that almost the entire operation time is in the transient state. In other words, it is assumed that the operation period of the first resonance operation mode is set to 0.16 seconds and the operation period of the second resonance operation mode is set to 0.09 seconds so that the stable operation period of each of the first and second resonance operation modes is, for example, 0.02 seconds. The operation state of the brush in this case is shown in FIG. 9D. With this setting, the transient state period may take up almost the entire operation period (0.21/0.25).

In this manner, a variety of operations can be realized by setting the switching intervals as appropriate.

As described above, in accordance with the present invention, the transient state during switching between a plurality of resonance operation modes having respective different resonance directions is used to realize irregular brush vibration thereby to improve the plaque removing power and sense of medical treatment. The use of resonance increases the vibration amplitude of the brush in the transient state. In addition, the operating time at a high frequency for obtaining the plaque removing effect is reduced, so that stimuli to gums can be alleviated. Moreover, since a plurality of resonance operation modes are realized only by motor rotational speed control, no special mechanism or component is required in the driving system or the transmission system. Therefore, complication of the structure and cost increase of the electric toothbrush are not caused. Furthermore, the use of the resonance phenomenon can increase the amplitude (improve the plaque removing power) with power consumption equivalent to that of the normal operation mode and is thus effective.

Second Embodiment

Figure 10:
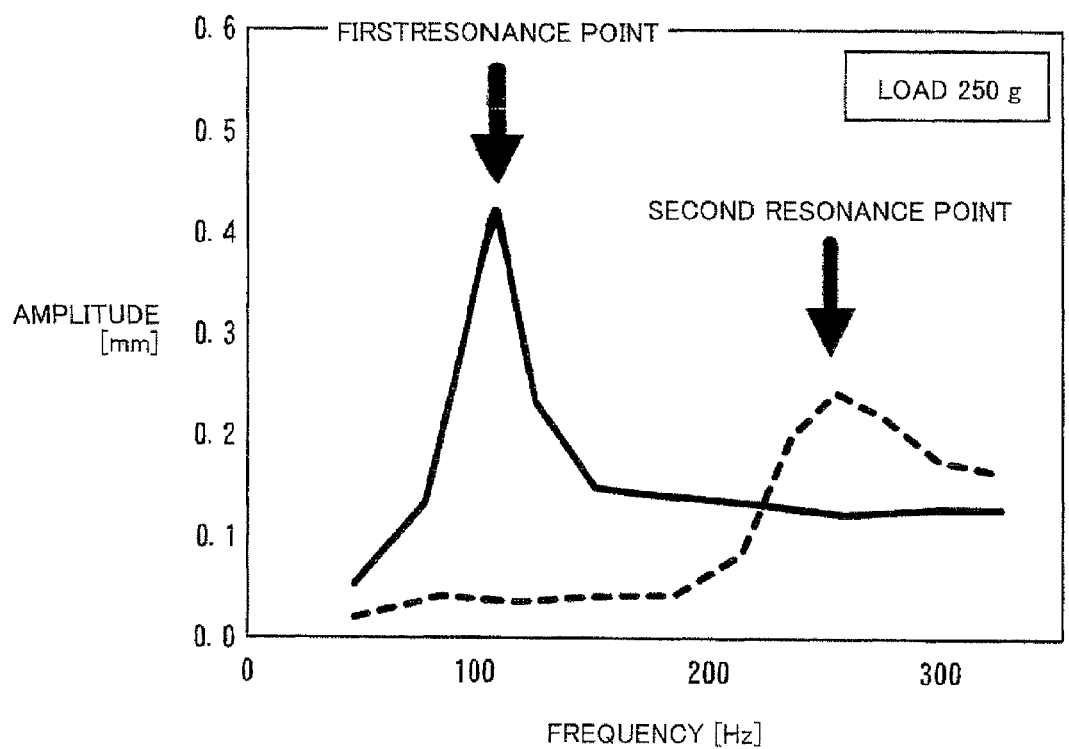
FIG. 10 is a graph showing resonance points in a case of a load 250 g.

In the foregoing first embodiment, a single setting value is used in each operation mode. However, as shown in FIG. 10, when a load acting on the brush changes, the vibration characteristic of the brush varies and the position of the resonance point is changed. FIG. 10 shows the vibration characteristic in the case of a load of 250 g, where the first resonance point appears in the neighborhood of 110 Hz and the second resonance point appears in the neighborhood of 250 Hz. It can be understood that both resonance points increase as compared with the case of a load of 100 g (FIG. 5). In the second embodiment, therefore, a load acting on the brush is sensed so that the rotational speed of the motor is adjusted in accordance with the magnitude of the load.

Figure 11:
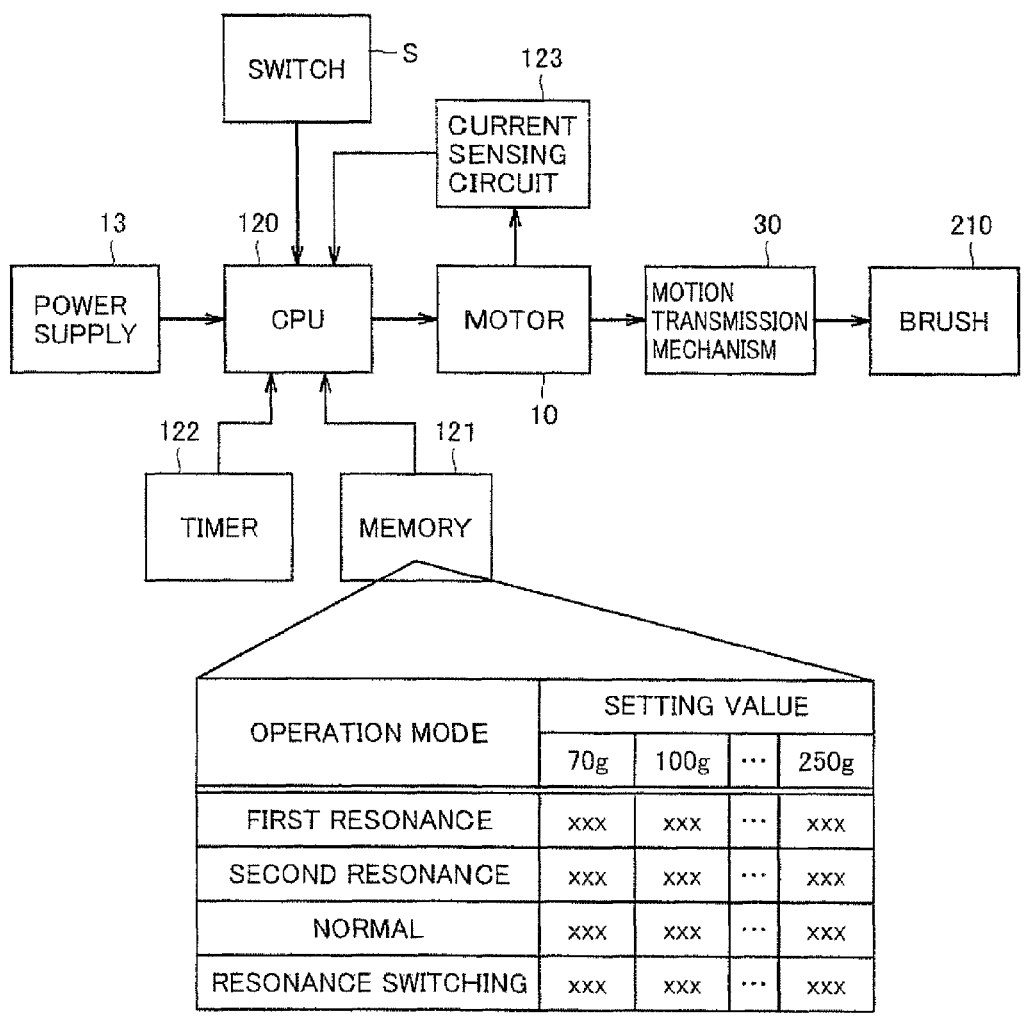
FIG. 11 is a block diagram in accordance with a second embodiment.

FIG. 11 is a block diagram of the electric toothbrush in the second embodiment. It differs from the first embodiment in that a current sensing circuit 123 is provided and that a plurality of setting values corresponding to the magnitudes of loads are stored in memory 121.

Current sensing circuit 123 is a circuit for sensing a current value of motor 10. The stronger the brush is pushed against a tooth surface, the greater the load acting on the brush becomes. Then, as the load acting on the brush increases, the load of motor 10 also increases and the value of current flowing through motor 10 increases. Therefore, CPU 120 can estimate the magnitude of the load acting on brush 210, based on the sensing result obtained from current sensing circuit 123.

Setting values corresponding to loads ranging from 70 g to 250 g are stored in memory 121 for each operation mode. In the present embodiment, respective setting values corresponding to values (representative values) of predetermined loads, such as loads of 70 g, 100 g, . . . , 250 g, are prepared. CPU 120 selects the optimum one of these setting values based on the value of the load acting on the brush or calculates a proper value by interpolating these setting values. In a case where a setting value can be expressed by a function of magnitude of a load, it is also preferable that a parameter representing the function is stored in the memory.

When the value of the load changes, the period of the transient state during switching of each operation mode also varies. Therefore, in the resonance switching operation mode, a proper value of the switching interval of each mode is also changed. Then, the switching intervals corresponding to the values of load are also stored in memory 121.

With such a configuration, the rotational speed of the motor is adjusted as appropriate in accordance with the magnitude of the load acting on the brush, so that a shift of resonance point dependent on the load can be compensated for and the resonance phenomenon can be duplicated precisely. In addition, the proportion of the transient state period in the entire operation period can also be duplicated precisely.

Third Embodiment

In the present embodiment, considering that the vibration characteristics vary depending on the kind of brush, the kind of brush part 21 that is currently attached is detected, and the vibration characteristics corresponding to the detected kind is used. In order to detect the kind of brush, an identification marker that differs according to the kind of brush is provided on brush part 21. An identification marker reading unit is provided on body 1 for detecting the kind of brush.

The identification marker may be formed of a conductive material having a resistance value that differs depending on the kind of brush. The identification marker reading unit of body 1 can determine the kind of brush by reading the resistance value of the conductive material.

Alternatively, the identification marker may be formed of an electromagnetic element such as a permanent magnet. The intensity of magnetic field applied to the identification marker reading unit when the brush is attached is varied by changing the intensity of magnetic force of the magnet or the magnet installation position according to the kind of brush. The identification marker reading unit of body 1 includes a coil to detect the intensity of induced electromotive force caused when brush part 21 is attached. Since the intensity of induced electromotive force is proportional to the intensity of the magnetic filed applied to the coil, the brush kind can be determined based on the induced electromotive force.

Alternatively, the identification marker reading unit may be formed of a plurality of photosensitive elements, and the identification marker may be formed of hole portions located at the positions corresponding to the photosensitive elements. The locations of the holes are varied depending on the kind of brush, so that the identification marker reading unit can determine the brush kind by from which of the photosensitive elements light is received. In a case where there are three photosensitive elements, eight states (seven kinds of brushes and the non-attached state) can be identified.

Alternatively, the identification marker reading unit may be formed of a plurality of photosensitive elements that can sense different kinds of wavelengths, and the identification marker may be formed of an optical filter element that transmits light having a particular wavelength. The wavelength transmitted through the filter is varied depending on the kind of brush so that the brush kind can be determined.

Alternatively, the identification marker reading unit may be formed of a plurality of mechanical switches, and the identification marker may be a slit-like notch or hole provided at the position corresponding to each switch. The location of the notch or hole is varied depending on the brush kind, so that the position of the switch that is switched at a time of attachment is varied. Therefore, the brush kind can be determined by determining which switch is switched.

In this manner, the kind of the attached brush part 21 can be determined using the identification marker. Therefore, the vibration characteristics for a variety of brush kinds are stored in memory 121 so that the vibration characteristic corresponding to the kind of the attached brush can be used. Furthermore, in addition to the vibration characteristics, the operation mode may be varied among brush kinds. In other words, the plaque removing effect can be optimized in accordance with the kind of the attached brush.

It is noted that whether brush part 21 is attached or not can be determined using the mechanisms as described above. Therefore, control can be performed such that even when the power button is pressed, the power is not turned on in a state in which brush part 21 is not attached. In recent years, while electric toothbrushes are reduced in size and are convenient to carry, they may be powered on unintentionally by unexpected external force while being carried or kept in the bag, etc., thereby giving annoying operating noise or vibration and consuming battery power. Such problems can be eliminated by prohibiting power-on in a state in which brush part 21 is not attached as described above.

Furthermore, another mechanism for preventing the above-noted unintentional power-on may be as follows. Specifically, a key-lock mode may be employed in which long pressing the power button prevents a button operation from being accepted. In addition, a button operation for unlocking is registered beforehand by the user so that the key is unlocked to enable power-on only when this operation is performed during locking of the key. An available unlocking operation pattern may be, for example, to press the power button three times in one second followed by long pressing for longer than one second. The user performs this operation beforehand and the resulting signal pattern is then stored. Then, when a signal having a pattern that matches the stored one is input during locking of the key, the key is unlocked. Since there is a low possibility that such a complicated operation is unintentionally done, unintentional power-on can be prevented. The unlocking operation may not be an operation of a single button but may be an operation pattern of a plurality of buttons.

Modification

The configurations of the foregoing embodiments are only illustrated as examples of the present invention. The numerical values used in the foregoing description are shown only by way of illustration and do not restrict the present invention. The scope of the present invention is not limited to the foregoing embodiments and various modifications can be made within the scope of the technical idea thereof.

In the resonance switching operation mode in the foregoing embodiments, the first resonance operation mode and the second resonance operation mode are alternately switched. The switching manner, however, is not limited thereto. It can be assumed that the cause of irregular brush trajectory in the transient state lies in that the trajectories of the brush in the stable operation state are different between before and after switching. Therefore, the similar effect as in the foregoing embodiments can be brought about as long as switching takes place between operation modes having brush operation trajectories different from each other.

For example, the first resonance operation mode and the normal operation mode may be alternately switched, or the second resonance operation mode and the normal operation mode may be alternately switched. If the resonance operation mode is included either before or after switching in this manner, a brush motion having a large amplitude which uses resonance at least temporarily can be obtained. Switching at high speed may be performed between the normal operation modes which do not use resonance. The irregular brush motion in the transient state is also obtained in this case. Furthermore, even when the driving frequency is not a resonance frequency, if the driving frequency is switched before and after the resonance frequency, it passes through the resonance frequency in the transient state, so that the amplitude of the brush can be increased in the transient state.

Although switching takes place between two operation modes in the resonance switching operation mode in the foregoing embodiments, switching may take place between three or more operation modes. For example, a switching manner in which the normal operation mode is sandwiched between two resonance operation modes or a switching manner in which those plurality of operation modes are switched at random is also preferable. Furthermore, a third resonance point of the brush is used so that switching takes place at high speed between three operation modes using resonance. In this case, switching may take place at high speed between any two operation modes selected from the three resonance points, or the three operation modes may be switched in order, or the three operation modes may be switched at random.

Furthermore, the operation mode such as the first resonance operation mode or the second resonance operation mode in which only one resonance point is used may be eliminated, and only an operation mode such as the resonance switching mode in which a plurality of resonance points are switched at high speed may be employed.

The invention claimed is:
1. An electric toothbrush comprising:
a driving source;
a vibrating member having a brush;

a motion transmission mechanism for converting output of said driving source into vibration of said vibrating member; and control means for controlling output of said driving source, by repetitively switching a driving frequency of said vibrating member at high speed between a plurality of different frequencies to utilize brushing during transition at said switches of said driving frequency.

2. The electric toothbrush according to claim 1, wherein at least one of said plurality of different frequencies is a resonance frequency of said vibrating member.

3. The electric toothbrush according to claim 2, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

4. The electric toothbrush according to claim 1, wherein
said vibrating member has a first resonance point in which said brush resonates in a first direction and a second resonance point in which said brush resonates in a second direction, and
said plurality of different frequencies include a frequency corresponding to said first resonance point and a frequency corresponding to said second resonance point.

5. The electric toothbrush according to claim 4, wherein said control means alternately switches output such that said vibrating member is repeatedly driven between the frequency corresponding to said first resonance point and the frequency corresponding to said second resonance point.

6. The electric toothbrush according to claim 5, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

7. The electric toothbrush according to claim 4, wherein said control means
has a first operation mode in which output of said driving source is controlled such that resonance in said first direction is produced and a second operation mode in which output of said driving source is controlled such that resonance in said second direction is produced, and said control means repeats the first and second operation modes at high speed.

8. The electric toothbrush according to claim 7, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

9. The electric toothbrush according to claim 4, wherein said first direction is a direction parallel to a brush face, and said second direction is a direction vertical to said brush face.

10. The electric toothbrush according to claim 9, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

11. The electric toothbrush according to claim 4, wherein
said first resonance point is characterized by being dependent on said motion transmission mechanism, and
said second resonance point is characterized by being dependent on said brush.

12. The electric toothbrush according to claim 11, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

13. The electric toothbrush according to claim 4, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

14. The electric toothbrush according to claim 1, wherein a trajectory of a brush operation corresponding to a driving frequency before switching is different from a trajectory of a brush operation corresponding to a driving frequency after switching.

15. The electric toothbrush according to claim 14, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

16. The electric toothbrush according to claim 1, wherein
a period during which an operation of the brush is stable is a stable operation period, and a period from switching of a driving frequency until an operation of the brush becomes stable is a transient state period, and
said control means switches a driving frequency such that the transient state period is equal to or longer than one third of the stable operation period.

17. The electric toothbrush according to claim 16, wherein said control means switches a driving frequency such that the transient state period is equal to or longer than the stable operation period.

* * * * *